United States Patent
Sun et al.

(12) 
(10) Patent No.: US 6,730,477 B1
(45) Date of Patent: May 4, 2004

(54) METHOD OF DIAGNOSING, MONITORING AND STAGING BREAST CANCER

(75) Inventors: Yongming Sun, San Jose, CA (US); Susana Salceda, San Jose, CA (US); Herve Recipon, San Francisco, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/664,249

(22) Filed: Sep. 18, 2000

Related U.S. Application Data

(63) Continuation-in-part of application No. PCT/US99/16811, filed on Jul. 22, 1999.
(60) Provisional application No. 60/095,232, filed on Aug. 4, 1998.

(51) Int. Cl.[7] .............................. C12Q 1/68; G01N 33/53
(52) U.S. Cl. .............................................. 435/6; 435/7.1
(58) Field of Search ........................... 435/6, 7.1, 91.2; 424/1.49, 174.1; 536/23.5, 24.31

(56) References Cited

U.S. PATENT DOCUMENTS

| | | | |
|---|---|---|---|
| 5,668,267 A | 9/1997 | Watson et al. | 536/23.5 |
| 5,759,776 A | 6/1998 | Smith et al. | 435/6 |

FOREIGN PATENT DOCUMENTS

| | | |
|---|---|---|
| WO | WO 98/18945 | 7/1998 |
| WO | WO 99/02559 | 1/1999 |
| WO | WO 00/08210 A1 | 2/2000 |
| WO | WO 00/43421 A1 | 7/2000 |
| WO | WO 00/60076 A2 | 10/2000 |
| WO | WO 00/62736 A2 | 10/2000 |
| WO | WO 00/73801 A2 | 12/2000 |
| WO | WO 00/78960 A2 | 12/2000 |

OTHER PUBLICATIONS

Griffin et al., "Initial Clinical Study of Indium–111–Labeled Clone 110 Anticarcinoembryonic Antigen Antibody in Patients with Colorectal Caner", *J. Clin. Onc.* 1991 9:631–640.

Lauffer, R.B., "Targeted Relaxation Enhancement Agents for MRI*", *Magnetic Resonance in Medicine* 1991 22:339–342.

Rosenberg, S. A. et al., "Use of Tumor–Infiltrating Lymphocytes and Interleukin–2 In the Immunotherapy of patients with Metastatic Melanoma", 1988 *N. England J. Med.* 319:1676–1680.

Sumerdon et al., "An Optimized Antibody–Chelator Conjugate for Imaging of Carcinoembryonic Antigen with Indium–111", *Nucl. Med. Biol.* 1990 17:247–254.

DATABASE EMBL ebi; Aug. 6, 1995 Hillier et al., "The WashU–Merck EST Project", Database accession No. r83119 XP002005119.

DATABASE EMBL ebi; Jul. 12, 1995 Hillier et al., "The WashU–Merck EST Project", Database accession No. h26328 XP002205120.

*Primary Examiner*—Kenneth R. Horlick
(74) *Attorney, Agent, or Firm*—Licata & Tyrrell P.C.

(57) ABSTRACT

The present invention provides a new method for detecting, diagnosing, monitoring, staging, and prognosticating breast cancer.

13 Claims, No Drawings

SEQUENCE LISTING

```
<160> NUMBER OF SEQ ID NOS: 10

<210> SEQ ID NO 1
<211> LENGTH: 544
<212> TYPE: DNA
<213> ORGANISM: Homo sapiens
<220> FEATURE:
<221> NAME/KEY: unsure
<222> LOCATION: (505)..(506)
<223> OTHER INFORMATION: a, c, g or t
<220> FEATURE:
<221> NAME/KEY: unsure
<222> LOCATION: (510)
<223> OTHER INFORMATION: a, c, g, or t
<220> FEATURE:
<221> NAME/KEY: unsure
<222> LOCATION: (521)
<223> OTHER INFORMATION: a, c, g or t
<220> FEATURE:
<221> NAME/KEY: unsure
<222> LOCATION: (527)..(528)
<223> OTHER INFORMATION: a, c, g, or t
<220> FEATURE:
<221> NAME/KEY: unsure
```

```
<222> LOCATION: (531)
<223> OTHER INFORMATION: a, c, g or t
<220> FEATURE:
<221> NAME/KEY: unsure
<222> LOCATION: (534)..(535)
<223> OTHER INFORMATION: a, c, g or t
<220> FEATURE:
<221> NAME/KEY: unsure
<222> LOCATION: (540)
<223> OTHER INFORMATION: a, c, g or t
<220> FEATURE:
<221> NAME/KEY: unsure
<222> LOCATION: (541)
<223> OTHER INFORMATION: a, c, g or t

<400> SEQUENCE: 1
ctagtctcga gtctagagcg ccttgccttc tcttaggctt tgaagcattt ttgtctgtgc      60
tccctgatct tcatgtcacc accatgaagt tcttagcagt cctggtactc ttgggagttt    120
ccatctttct ggtctctgcc cagaatccga caacagctgc tccagctgac acgtatccag    180
ctactggtcc tgctgatgat gaagcccctg atgctgaaac cactgctgct gcaaccactg    240
cgaccactgc tgtccctacc actgcaacca ccgctgcttc taccactgct cgtaaagaca    300
ttccagtttt acccaaatgg gttggggatc tcccgaatgg tagagtgtgt ccctgagatg    360
gaatcagctt gagtcttctg caattggtca caactattca tgcttcctgt gatttcatcc    420
aactacttac cttgcctacg atatcccctt tatctctaat cagtttattt tctttcaaat    480
aaaaaataac tatgagcaac taannaaaan aaaaaaaaaa naaaannaa naannaaaan     540
naga                                                                  544

<210> SEQ ID NO 2
<211> LENGTH: 1066
<212> TYPE: DNA
<213> ORGANISM: Homo sapiens
<220> FEATURE:
<221> NAME/KEY: unsure
<222> LOCATION: (729)..(813)
<223> OTHER INFORMATION: a, c, g or t

<400> SEQUENCE: 2
gttgaccagt ggtcatgcca ctgcctgttg atttgttgaa atatattgttt acacgtatgt    60
ytcttgttact gattgtcaga aagctggttt tgagactgca gcttggacta aattcagtca   120
tctggctgtc tggggaagca tgctgaccag tctggtgttc tttggcatct actcagccat    180
ctggtccacc attctcattg ccccaaatat gagaggacaa agaatggta ccggtactgc     240
caatggagat ggaggaagga gacagaaaga aacagagccc agaccctagg gaccaccagc   300
atttgcagaa tggataaaca gccttcttcc taacaaagga agcacagcaa ctgtgatcct   360
gagctgtgca cacttctggt tgggattatt tctggtttct acttcctgtt gaagatgtg    420
gcatggagag tgaacaagct gctgcccacc acctggcatc acagcccag aactcagcta    480
tttccatggg accacagcat ctcatctctg ggctgagcca gaaagacccc tactgaagtc   540
cagaggcact tttctgaaag gctctgcttt gacctgaagt atttatcta tcctcagtct    600
caggacactg ttgatggaat taaggccaag cacatctgca aaaagacat tgctggagga   660
ggtgcaaaga gctggaaacc aagtctccag tcctgggaaa agcagtggta tggaaaagca   720
atggaaagnn nnnnnnnnnn nnnnnnnnnn nnnnnnnnnn nnnnnnnnnn nnnnnnnnn     780
nnnnnnnnnn nnnnnnnnnn nnnnnnnnnn nnncatagca ccaatgacct gaagagcctt   840
gttgaaggaa gactccatct gatgactcag agcaagtatt ttttagtgtg ttattgttat   900
```

-continued

| | |
|---|---|
| tagcagaaag agggccataa aatacatggg gcaagctgaa tatatcttag gcaaaagaag | 960 |
| aaaatattca aattcttatg ttattttatc taattatttt atctcttttt gtgtgtgact | 1020 |
| tataatgtgt gtattgtatt aataaaagta tataaacatg tagttt | 1066 |

<210> SEQ ID NO 3
<211> LENGTH: 4197
<212> TYPE: DNA
<213> ORGANISM: Homo sapiens

<400> SEQUENCE: 3

| | |
|---|---|
| ggcacgagac aactcatgct aggaggccag tcctagcatc accttatgtt gaaaatctta | 60 |
| ccaatagtct gtgtcaacag aatacttatt ttagaagaaa aattcatgat ttcttcctga | 120 |
| agcctacaga cataaaataa cagtgtgaag aattacttgt tcacgaattg cataaagctg | 180 |
| cacaggattc ccatctaccc tgatgatgca gcagacatca ttcaatccaa ccagaatctc | 240 |
| gctctgtcac tcaggctgga gtgcagtggc gcaatctcgg ctcactgcaa actctgcctc | 300 |
| ccaggttcac gccattctcc tgccacagcc tcccgagtag ctgggactac aggcgcccgc | 360 |
| caccaagcac agctaagttt tttatttata gtagagacgg ggtttcactg tgttagccag | 420 |
| gatggtctcg atctcctgac ctcgtgatct gcctgcctcg gcctcccaaa gtgccgggat | 480 |
| tacaggcgtg agccaccgcg ccgggcctga tttcagtttc ttccagccct tcctattgtt | 540 |
| aacatggggg ttgtgttgaa gaatataaag ttacaaagtc aaggaagtag gaaacatttt | 600 |
| tacaagtatt atgtagccat cttggtgggg ctgtggtgag gtaggctgca aatgattctc | 660 |
| ctatttcttt ccctgagttc agaacatagg aattagattg atagacatca acatacccgc | 720 |
| tttattgctg actcatgaca actaatggga agacatggct cagatgtgca gccacagtga | 780 |
| gcttctgaac atttcttctc agactaagct cttacacaca gttgcagttg aagaaagaa | 840 |
| ttgcttgaca tggccacagg agcaggcagc ttcctgcaga catgacagtc aacgcaaact | 900 |
| catgtcactg tgggcagaca catgtttgca aagagactca gagccaaaca agcacactca | 960 |
| atgtgctttg cccaaattta cccattaggt aaatcttccc tcctcccaag aagaaagtgg | 1020 |
| agagagcatg agtcctcaca tggaaacttg aagtcaggga aatgaaggct caccaattat | 1080 |
| ttgtgcatgg gtttaagttt tccttgaaat taagttcagg tttgtctttg tgtgtaccaa | 1140 |
| ttaatgacaa gaggttagat agaagtatgc tagatggcaa agagaaatat gttttgtgtc | 1200 |
| ttcaattttg ctaaaaataa cccagaacat ggataattca tttattaatt gattttggta | 1260 |
| agccaagtcc tatttggaga aaattaatag ttttttctaaa aagaattttt ctcaatatca | 1320 |
| cctggcatga taacattttt ctccttcgag ttccttttc tggagtttaa caaacttgtt | 1380 |
| ctttacaaat agattatatt gactacctct cactgatgtt atgatattag tttctattgc | 1440 |
| ttactttgta tttctaattt taggattcac aatttagctg gagaactatt ttttaacctg | 1500 |
| ttgcacctaa acatgattga gctagaagac agttttacca tatgcatgca ttttctctga | 1560 |
| gttatatttt aaaatctata catttctcct aaatatggag gaaatcactg gcatcaaatg | 1620 |
| ccagtctcag acggaagacc taaagcccat ttctggcctg gagctacttg gctttgtgac | 1680 |
| ctatggtgag gcataagtgc tctgagtttg tgttgcctct tttgtaaaat gagggtttga | 1740 |
| cttaatcagt gattttcata gcttaaaatt tttttgaaga acagaacttt ttttaaaaac | 1800 |
| agttagatgc aaccatatta tataaaacag aacagataca agtagagcta acttgctaaa | 1860 |
| gaaaggatgg aggctctgaa gctgtgactt cattatccct taatactgct atgtcctctg | 1920 |
| tagtaccttg gatttctatg ggacatcgtt taaaaactat tgtttatgcg agagccttgc | 1980 |

```
taatttccta aaaattgtgg atacattttt tctcccatgt ataattttct caccttctat    2040
ttaaaaagaa aaaaaaagtc agtgtagtat ttacatattt taccctataa ggagctaaca    2100 taactttga tttagtgtta ttcataaaat taggttagca gtttattaac cttttgtatt     2160
```
(taactttga: as shown)

```
tgctctggca atgtttaata tctcataagc tatacacacc tcgaagccat caatgacaac    2220
cttttcttgc tgaatagaac agtgattgat gtcatgaaga caattttatc tccttttgcc    2280
ttccataatt tgtaccaggt tatataatag tataacactg ccaaggagcg gattatctca    2340
tcttcatcct gtaattccag tgtttgtcac gtggttgttg aataaatgaa taagaatga     2400 gaaaaccaga agctctgata cataatcata atgataatta tttcaatgca caactacggg    2460
tggtgctgaa ctagaatcta tattttctga aactggctcc tctaggatct actaatgatt    2520
taaatctaaa agatgaagtt agtaaagcat cagaaaaaaa aggtaaacaa attgctcctg    2580
tggagatgat tggcatcaca tggtgttttg agctgataca cccaacactt gagctcactg    2640
caacagtacc agattttcac cgctatgcct cctttcactc tgggagtctt ccagaggtct    2700
tgcactcggg agagcatgct caggtttccc cagctctaca aaatcaccca gaatgccaaa    2760
gacttcaaca caagggtaaa taaggttgat ctcagaattg tcacctcaaa aaggccctgc    2820
cttccactgt tcagttctgg tcatctgcct atgagatatc tgaagcttga aagagaacac    2880
ttgaaaatca ctgagaccgt gactcccatc ccagcacaca cagcaagcca aagtccacac    2940
catggaaacc gattcctcat cttttaagaa taccatatgg atacttatat ataggcatga    3000
attaagcaac taggcctttc aacagttttg gagaaggcca tttcccactt ttaaaataaa    3060
taatgctcct ataagatcag atactgtgtt gaccagtggt catgccactg cctgttgatt    3120
tgttgaaaat attgtttaca cgtatgttct tgttactgat tgtcagaaag ctggttttga    3180
gactgcagct tggactaaat tcagtcatct ggctgtctgg ggaagcatgc tgaccagtct    3240
ggtgttcttt ggcatctact cagccatctg gtccaccatt ctcattgccc caaatatgag    3300
aggacagatt aacaatggta ccagcacgtg cagaaaagaa agagtctccg cttgtctttg    3360
tctgattctc ctgtcctctc catggaagtt acattttctg taaaggatga gctgaaaatt    3420
ctcctggtcg ttgccagttg aacttctgct gtgctctggg aaggcattct cactctgttt    3480
atgttgtcta agtgcagaca tggatgtgca ggtttgctag aacctcctga ggatgtgcaa    3540
tggttctgtt catgcctgaa tcagttcttt tgggagtgga cattctttct ctccctcatg    3600
cacagcctca ggcacatggc ttgagctatg gcggcacgca gtatgccat cacccaggta     3660 caccccttcc ctaagaagag gctcttcagg ttacactcgg gtactgttgt tatctggctt    3720
attgtccata ggatcaacat agagtcctga ggtcagttca aaccatcaaa ccagggatgt    3780
tacttattat ttgaaaactt ctttggaaag ataatcttgg gttgttcagt gggaccagtc    3840
tttgacgggc aaatctccag aatacatggg gtcagttctc tcaggttcag gaagcatgta    3900
atctctctaa gattcattaa ttaaaaaaaa aagacacatg catagaaaaa tagaacaaaa    3960
tggaaactct ttattggata cctactatgg gttatgtgcc agggtttcct aatcatttgg    4020
ggacatgtgt gtataaacaa aaccaggcta tgtggccagg cagtgtgtgg ctcacacctg    4080
taatcccagt gctagggaa gccaagttgc aaggatcgct tgaaaccagg agttcgagac     4140
tagcctgggc aacatagtga gacccggtct ctgcaaaaaa aaaaaaaaaa aaaaaa        4197
```

<210> SEQ ID NO 4
<211> LENGTH: 1560
<212> TYPE: DNA

<213> ORGANISM: Homo sapiens

<400> SEQUENCE: 4

```
agctcaatac ggaacatatt ctcagtcctc ctctggtcta caaagcctgt gatttcttgt      60
ctatggacag aacgtctggt ttaatctaca ggaacccata acttcctgaa gctttatgct     120
taacagtgac aacgtgagtc agttgaattt tattgtgttt cagtccgtag agtattagct     180
acagaaacct ttccattgcc atactgagaa actggcagca ggcagtgtgc ctacaggtct     240
acaaagaaac ttcagatcat cttcttgagg gaaagaagct gaagtgctac ataagatgct     300
tgtgcttcat aactctcaga agctgcagat tctgtataaa tccttagaaa agagcatccc     360
tgaatccata aaggtatatg gcgccatttt caacataaaa gataaaaacc ctttcaacat     420
ggaggtgctg gtagatgcct ggccagatta ccagatcgtc attacccggc tcagaaaca      480
ggagatgaaa gatgaccagg atcattatac caacacttac cacatcttca ccaaagctcc     540
tgacaaatta gaggaagtcc tgtcatactc caatgtaatc agctgggagc aaactttgca     600
gatccaaggt tgccaagagg gcttggatga agcaataaga aaggttgcaa cttcaaaatc     660
agtgcaggta gattacatga aaaccatcct ctttataccg gaattaccaa agaaacacaa     720
gacctcaagt aatgacaaga tggagttatt tgaagtggat gatgataaca aggaaggaaa     780
cttttcaaac atgttcttag atgcttcaca tgcaggtctt gtgaatgaac actgggcctt     840
tgggaaaaat gagaggagct tgaaatatat tgaacgctgc ctccaggatt ttctaggatt     900
tggtgtgctg ggtccagagg gccagcttgt ctcttggatt gtgatggaac agtcctgtga     960
gttgagaatg ggttatactg tccccaaata cagacaccaa gcaacatgt tgcaaattgg     1020
ttatcatctt gaaaagtatc tttctcagaa agaaatccca tttatttcc atgtggcaga     1080
taataatgag aaaagcctac aggcactgaa caatttgggg tttaagattt gtccttgtgg    1140
ctggcatcag tggaaatgca cccccaagaa atattgttga ttgattccac tgtccatttc    1200
aaatctttct tatcagtaaa aaaacattaa ttcaaacaca agcattgtga tctacattag    1260
cacaaaatgc aactgattat ctaggatctg tgtattactt aagctcaccc ttaacagttt    1320
taccttcctt ctcctctgta ttcttacaga aaattagaag ctcaattta tggtctcata    1380
atttcctta tgcagacat ctcagaatta aaatcaccca agccaatca ttagtgccaa     1440
gataaccctt taacgggcaa cactttctta aatgaagact atttctttca tgaaaaatt    1500
cacttttatg actttcttgt taaaataaaa agtctgcttt taaaaaaaaa aaaaaaaaa     1560
```

<210> SEQ ID NO 5
<211> LENGTH: 1227
<212> TYPE: DNA
<213> ORGANISM: Homo sapiens
<220> FEATURE:
<221> NAME/KEY: unsure
<222> LOCATION: (327)
<223> OTHER INFORMATION: a, c, g or t
<220> FEATURE:
<221> NAME/KEY: unsure
<222> LOCATION: (352)
<223> OTHER INFORMATION: a, c, g or t
<220> FEATURE:
<221> NAME/KEY: unsure
<222> LOCATION: (369)
<223> OTHER INFORMATION: a, c, g or t
<220> FEATURE:
<221> NAME/KEY: unsure
<222> LOCATION: (850)..(880)
<223> OTHER INFORMATION: a, c, g or t
<220> FEATURE:
<221> NAME/KEY: unsure
<222> LOCATION: (1220)
<223> OTHER INFORMATION: a, c, g or t

<400> SEQUENCE: 5

```
attttgtagt tcagcaaatc ctccaaatac acagcatgtt acaaggcact ggtggcacag      60
ggcacaacag gaaatgatat ttatttagca aattcattta acaaatatta ttgggcacct     120
gttatgtgag acactgtcct aggcactgtg ggataacaac agcaaacact tcacacaaca     180
gcctggcctt cctgtgtttt acaacagctc ctaaagatag ctgatatcaa gacatttgag     240
ggacacagtt catgtagaat caaaatatta gtatttcaga ataaggattt tttttctgaa     300
aagcatacag agaggaaaca gcttaanaat aggtcaagac ctaaaaacag antataatca     360
cggaataanc tggataaccc agacagtccc cacagaattt ctttcaggtc acagatttct     420
taaaactcac ccccaaaatg tgcctgcttg gttgtttgaa tcttgcataa ttaatgtcac     480
aggcgcaagc cgctgaactt agttgagatg cagaaaacaa acaaatgcaa tgacatatct     540
gagaagcatt tatgtaactc cggttaagtg gtgaggaggg gtgtgtgaag acagtgtgca     600
tgcatgagtg tgtattcata tatatgtgta tacatatgaa tttcactgtt attttccagg     660
gtctatggac aatgtggcag taagagtcta tgatgttctg aaacttttca cagtaaatcc     720
aaagattaca gaccttacaa ggtgcttgca ttctgttgct tttccatctg tcacttctca     780
ggttatttga ctgtgttcaa accttctttt ctttttcatt gagtttcatt ttttaagctt     840
gttaaatgcn nnnnnnnnnn nnnnnnnnnn nnnnnnnnnn tgtcattttt cacattatcc     900
tctcttctct gcaacaagga tagtaagatg tagatgaatg caaaaataat aacaacaata     960
aggaaatata ttaaagcttt aaaatatgca catatgtagt tctaaagagc aataacggta    1020
gtatctattt cgaacatgca ttaggcaaaa aagaaatcaa aactgaaatt ttcgtgtatt    1080
tttccccttg taagatgttc aaatgctaac ttcatttttct cctttcctct atgtggcact   1140
ttctcaaaat atctatgaaa tacttttaga caaagattga gctggagaaa gagatacaaa    1200
tttccatccc cccagacagn gagacat                                         1227
```

<210> SEQ ID NO 6
<211> LENGTH: 253
<212> TYPE: DNA
<213> ORGANISM: Homo sapiens
<220> FEATURE:
<221> NAME/KEY: unsure
<222> LOCATION: (181)
<223> OTHER INFORMATION: a, c, g or t
<220> FEATURE:
<221> NAME/KEY: unsure
<222> LOCATION: (201)
<223> OTHER INFORMATION: a, c, g or t
<220> FEATURE:
<221> NAME/KEY: unsure
<222> LOCATION: (205)
<223> OTHER INFORMATION: a, c, g or t
<220> FEATURE:
<221> NAME/KEY: unsure
<222> LOCATION: (238)
<223> OTHER INFORMATION: a, c, g or t
<220> FEATURE:
<221> NAME/KEY: unsure
<222> LOCATION: (241)..(242)
<223> OTHER INFORMATION: a, c, g or t
<220> FEATURE:
<221> NAME/KEY: unsure
<222> LOCATION: (250)
<223> OTHER INFORMATION: a, c, g or t

<400> SEQUENCE: 6

| | |
|---|---:|
| gaacagcctc acttgtgttg ctgtcagtgc cagtagggca ggcaggaatg cagcagagag | 60 |
| gactcgccat cgtggccttg gctgtctgtg cggccctaca tgcctcagaa gccatacttc | 120 |
| ccattgcctc cagctgttgc acggaggttt cacatcatat ttccagaagg ctcctggaaa | 180 |
| nagtgaatat gtgtcgcatc naganagctg atggggattg tgacttggct gctgtcancc | 240 |
| nncatgtcan gcg | 253 |

```
<210> SEQ ID NO 7
<211> LENGTH: 943
<212> TYPE: DNA
<213> ORGANISM: Homo sapiens
<220> FEATURE:
<221> NAME/KEY: unsure
<222> LOCATION: (128)
<223> OTHER INFORMATION: a, c, g or t
<220> FEATURE:
<221> NAME/KEY: unsure
<222> LOCATION: (130)
<223> OTHER INFORMATION: a, c, g or t
<220> FEATURE:
<221> NAME/KEY: unsure
<222> LOCATION: (935)
<223> OTHER INFORMATION: a, c, g or t

<400> SEQUENCE: 7
```

| | |
|---|---:|
| gggggcctgg ccccggcccc tgtgaggacc ccgcgggtgc tggggtaaga ggctctagac | 60 |
| ccttcacctg tcagtcacct gagggaggct gaggccaagc cccatccctc agaatcaagg | 120 |
| cttgcaancn cccctcacct gcccagtctc tgtccacacc cctcgggctg aagacggccc | 180 |
| tgaccaggcc ctgggcctca gcgaccaccc ctcccctcc tgcctggacc cagggagcag | 240 |
| gtgcagggg ctccgagccc ctggtgactg tcaccgtgca gtgcgccttc acagtggccc | 300 |
| tgagggcacg aagaggagcc gacctgtcca gcctgcgggc actgctgggc caagccctcc | 360 |
| ctcaccaggc ccagcttggg caactcaggt gggccagaaa gccccggtg gctgcggtgg | 420 |
| agctgggcac cgccccgact gaggcagctg ctggaagagg gggtggcaga ggtcactgcc | 480 |
| ctccctgcag gccccaccca ggaggccccc tctgaggaat ctctttgcag ttacctagcc | 540 |
| ccaggtgagg acgggcactg gtccccatc cccgaggagg agtcgctgca gagggcctgg | 600 |
| caggacgcag ctgcctgccc caggggggctg cagctgcagt gcaggggagc cggggggtcgg | 660 |
| ccggtcctct accaggtggt ggcccagcac agctactccg cccaggggcc agaggacctg | 720 |
| ggcttccgac aggggacac ggtggacgtc ctgtgtgaag tggaccaggc atggctggag | 780 |
| ggccactgtg acggccgcat cggcatcttc cccaagtgct tcgtggtccc cgccggccct | 840 |
| cggatgtcag gagcccccgg ccgcctgccc cgatcccagc agggagatca gccctaatga | 900 |
| tgctgtgtcc atgatgcttt taatnaaaaa aacccccact gca | 943 |

```
<210> SEQ ID NO 8
<211> LENGTH: 249
<212> TYPE: DNA
<213> ORGANISM: Homo sapiens
<220> FEATURE:
<221> NAME/KEY: unsure
<222> LOCATION: (110)
<223> OTHER INFORMATION: a, c, g or t
<220> FEATURE:
<221> NAME/KEY: unsure
<222> LOCATION: (192)
<223> OTHER INFORMATION: a, c, g or t
<220> FEATURE:
<221> NAME/KEY: unsure
<222> LOCATION: (205)
<223> OTHER INFORMATION: a, c, g or t
```

<220> FEATURE:
<221> NAME/KEY: unsure
<222> LOCATION: (218)
<223> OTHER INFORMATION: a, c, g or t

<400> SEQUENCE: 8

```
atcacattaa gtcattgcta attttataaa caaaaacaat ggttttantt tgcatctccc      60
tgattggtat tgctgtagaa catatttgga gaagtttgtt tgtctttggn gtttatttca     120
tgaatagatt gtgtgcccat tttctcttgg ggtattcagt tttttattac tgatgtgagc     180
atgtgtatgg gngattattt gatgnttatc agttttgntt agtagactgg caatatttag     240
tcttgctgt                                                             249
```

<210> SEQ ID NO 9
<211> LENGTH: 690
<212> TYPE: DNA
<213> ORGANISM: Homo sapiens

<400> SEQUENCE: 9

```
gacgcccagt gacctgccga ggtcggcagc acagagctct ggagatgaag accctgttcc     60
tgggtgtcac gctcggcctg ccgctgccc tgtccttcac cctggaggag gaggatatca    120
cagggacctg gtacgtgaag gccatggtgg tcgataagga cttccggag acaggaggc    180
ccaggaaggt gtccccagtg aaggtgacag ccctgggcgg tgggaagttg aagccacgt    240
tcaccttcat gagggaggat cggtgcatcc agaagaaaat cctgatgcgg aagacggagg    300
agcctggcaa atacagcgcc tatgggggca ggaagctcat gtacctgcag gagctgccca    360
ggagggacca ctacatcttt tactgcaaag accagcacca tggggcctg ctccacatgg    420
gaaagcttgt gggtaggaat tctgatacca accgggaggc cctggaagaa tttaagaaat    480
tggtgcagcg caagggactc tcggaggagg acatttttcac gcccctgcag acgggaagct    540
gcgttcccga acactaggca gccccgggt ctgcacctcc agagcccacc ctaccaccag    600
acacagagcc cggaccacct ggacctaccc tccagccatg acccttccct gctcccaccc    660
acctgactcc aaataaagtc cttctccccc                                      690
```

<210> SEQ ID NO 10
<211> LENGTH: 294
<212> TYPE: PRT
<213> ORGANISM: Homo sapiens

<400> SEQUENCE: 10

```
Met Leu Val Leu His Asn Ser Gln Lys Leu Gln Ile Leu Tyr Lys Ser
  1               5                  10                  15

Leu Glu Lys Ser Ile Pro Glu Ser Ile Lys Val Tyr Gly Ala Ile Phe
             20                  25                  30

Asn Ile Lys Asp Lys Asn Pro Phe Asn Met Glu Val Leu Val Asp Ala
         35                  40                  45

Trp Pro Asp Tyr Gln Ile Val Ile Thr Arg Pro Gln Lys Gln Glu Met
     50                  55                  60

Lys Asp Asp Gln Asp His Tyr Thr Asn Thr Tyr His Ile Phe Thr Lys
 65                  70                  75                  80

Ala Pro Asp Lys Leu Glu Glu Val Leu Ser Tyr Ser Asn Val Ile Ser
                 85                  90                  95

Trp Glu Gln Thr Leu Gln Ile Gln Gly Cys Gln Glu Gly Leu Asp Glu
            100                 105                 110

Ala Ile Arg Lys Val Ala Thr Ser Lys Ser Val Gln Val Asp Tyr Met
```

-continued

```
                    115                 120                 125
Lys Thr Ile Leu Phe Ile Pro Glu Leu Pro Lys Lys His Lys Thr Ser
    130                 135                 140

Ser Asn Asp Lys Met Glu Leu Phe Glu Val Asp Asp Asp Asn Lys Glu
145             150                 155                     160

Gly Asn Phe Ser Asn Met Phe Leu Asp Ala Ser His Ala Gly Leu Val
                165                 170                 175

Asn Glu His Trp Ala Phe Gly Lys Asn Glu Arg Ser Leu Lys Tyr Ile
            180                 185                 190

Glu Arg Cys Leu Gln Asp Phe Leu Gly Phe Gly Val Leu Gly Pro Glu
        195                 200                 205

Gly Gln Leu Val Ser Trp Ile Val Met Glu Gln Ser Cys Glu Leu Arg
    210                 215                 220

Met Gly Tyr Thr Val Pro Lys Tyr Arg His Gln Gly Asn Met Leu Gln
225                 230                 235                 240

Ile Gly Tyr His Leu Glu Lys Tyr Leu Ser Gln Lys Glu Ile Pro Phe
                245                 250                 255

Tyr Phe His Val Ala Asp Asn Asn Glu Lys Ser Leu Gln Ala Leu Asn
            260                 265                 270

Asn Leu Gly Phe Lys Ile Cys Pro Cys Gly Trp His Gln Trp Lys Cys
        275                 280                 285

Thr Pro Lys Lys Tyr Cys
    290
```

METHOD OF DIAGNOSING, MONITORING AND STAGING BREAST CANCER

INTRODUCTION

This application is a continuation in part of PCT/US99/16811, filed Jul. 22, 1999, which claims the benefit of priority from U.S. provisional application Ser. No. 60/095,232, filed Aug. 4, 1998.

FIELD OF THE INVENTION

This invention relates, in part, to newly developed assays for detecting, diagnosing, monitoring, staging, prognosticating, imaging and treating cancers, particularly breast cancer.

BACKGROUND OF THE INVENTION

One of every nine American women will develop breast cancer sometime during her life based on a lifespan of 85 years. Annually, over 180,000 women in the United States will be diagnosed with breast cancer and approximately 46,000 will die of the disease.

Every woman is at risk for breast cancer. A woman's chances of developing breast cancer increase as she grows older; 80 percent of all cancers are found in women over the age of 50. There are also several risk factors that can increase a woman's chances of developing cancer. A woman may be at increased risk if she has a family history of the disease, if she had her first child after the age of 30 or has no children, or if she began menstruating early.

However, more than 70 percent of women who develop breast cancer have no known risk factors. Less than 10 percent of breast cancer cases are thought to be related to the BRCA1 gene discovered in 1994. Researchers are now investigating the role other factors such as nutrition, alcohol, exercise, smoking, and oral contraceptives may play in cancer prevention.

As with many other cancers, the best chance for successful treatment occurs when breast cancer is found early. Mammograms, special x-rays of the breast, can detect more than 90 percent of all breast cancers. If breast cancer is found early, the chance of cure is greater than 90 percent. Treatment options include surgery, chemotherapy, and radiation therapy depending on the stage of the cancer.

Procedures used for detecting, diagnosing, monitoring, staging, prognosticating and imaging breast cancer are of critical importance to the outcome of the patient. Patients diagnosed with early breast cancer generally have a much greater five-year survival rate as compared to the survival rate for patients diagnosed with distant metastasized breast cancer. New diagnostic methods which are more sensitive and specific for detecting early breast cancer are clearly needed.

Breast cancer patients are closely monitored following initial therapy and during adjuvant therapy to determine response to therapy and to detect persistent or recurrent disease of metastasis. There is clearly a need for a breast cancer marker which is more sensitive and specific in detecting breast cancer and its recurrence and progression.

Another important step in managing breast cancer is to determine the stage of the patient's disease. Stage determination has potential prognostic value and provides criteria for designing optimal therapy. Generally, pathological staging of breast cancer is preferable over clinical staging because the former gives a more accurate prognosis. However, clinical staging would be preferred were it at least as accurate as pathological staging because it does not depend on an invasive procedure to obtain tissue for pathological evaluation. Staging of breast cancer would be improved by detecting new markers in cells, tissues, or bodily fluids which could differentiate between different stages of invasion.

In the present invention methods are provided for detecting, diagnosing, monitoring, staging, prognosticating, imaging and treating breast cancer via breast specific genes referred to herein as BSGs. For purposes of the present invention, BSG refers, among other things, to native proteins expressed by the gene comprising the polynucleotide sequence of SEQ ID NO: 1, 2, 3, 4, 5, 6, 7, 8 or 9. An exemplary BSG protein sequence is depicted in SEQ ID NO:10. By "BSG" it is also meant herein polynucleotides which, due to degeneracy in genetic coding, comprise variations in nucleotide sequence as compared to SEQ ID NO: 1, 2, 3, 4, 5, 6, 7, 8 or 9, but which still encode the same protein. In the alternative, what is meant by BSG as used herein, means the native mRNA encoded by the gene comprising the polynucleotide sequence of SEQ ID NO: 1, 2, 3, 4, 5, 6, 7, 8 or 9, levels of the gene comprising the polynucleotide sequence of SEQ ID NO: 1, 2, 3, 4, 5, 6, 7, 8 or 9, or levels of a polynucleotide which is capable of hybridizing under stringent conditions to the antisense sequence of SEQ ID NO: 1, 2, 3, 4, 5, 6, 7, 8 or 9.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of breast cancer by analyzing for changes in levels of BSG in cells, tissues or bodily fluids compared with levels of BSG in preferably the same cells, tissues, or bodily fluid type of a normal human control, wherein a change in levels of BSG in the patient versus the normal human control is associated with breast cancer.

Further provided is a method of diagnosing metastatic breast cancer in a patient having such cancer which is not known to have metastasized by identifying a human patient suspected of having breast cancer that has metastasized; analyzing a sample of cells, tissues, or bodily fluid from such patient for BSG; comparing the BSG levels in such cells, tissues, or bodily fluid with levels of BSG in preferably the same cells, tissues, or bodily fluid type of a normal human control, wherein a change in BSG levels in the patient versus the normal human control is associated with a cancer which has metastasized.

Also provided by the invention is a method of staging breast cancer in a human which has such cancer by identifying a human patient having such cancer; analyzing a sample of cells, tissues, or bodily fluid from such patient for BSG; comparing BSG levels in such cells, tissues, or bodily fluid with levels of BSG in preferably the same cells, tissues, or bodily fluid type of a normal human control sample, wherein a change in BSG levels in the patient versus the normal human control is associated with a cancer which is progressing or regressing or in remission.

Further provided is a method of monitoring breast cancer in a human having such cancer for the onset of metastasis. The method comprises identifying a human patient having such cancer that is not known to have metastasized; periodically analyzing a sample of cells, tissues, or bodily fluid from such patient for BSG; comparing the BSG levels in such cells, tissue, or bodily fluid with levels of BSG in preferably the same cells, tissues, or bodily fluid type of a normal human control sample, wherein a change in BSG levels in the patient versus the normal human control is associated with a cancer which has metastasized.

Further provided is a method of monitoring the change in stage of breast cancer in a human having such cancer by looking at levels of BSG in a human having such cancer. The method comprises identifying a human patient having such cancer; periodically analyzing a sample of cells, tissues, or bodily fluid from such patient for BSG; comparing the BSG levels in such cells, tissue, or bodily fluid with levels of BSG in preferably the same cells, tissues, or bodily fluid type of a normal human control sample, wherein a change in BSG levels in the patient versus the normal human control is associated with a cancer which is progressing or regressing or in remission.

Further provided are methods of designing new therapeutic agents targeted to a BSG for use in imaging and treating breast cancer. For example, in one embodiment, therapeutic agents such as antibodies targeted against BSG or fragments of such antibodies can be used to treat, detect or image localization of BSG in a patient for the purpose of detecting or diagnosing a disease or condition. In this embodiment, a difference in the amount of labeled antibody detected as compared to normal tissue would be indicative of tumor metastases or growth. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable and therapeutic labels including, but not limited to, radioisotopes and paramagnetic metals. Therapeutic agents such as small molecules and antibodies which modulate the concentration and/or activity of BSG can also be used in the treatment of diseases characterized by altered expression of BSG. Such agents can be readily identified in accordance with teachings herein.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, prognosticating and imaging cancers by comparing levels of BSG with those of BSG in a normal human control. For purposes of the present invention, BSG refers, among other things, to native proteins expressed by the gene comprising the polynucleotide sequence of SEQ ID NO: 1, 2, 3, 4, 5, 6, 7, 8 or 9. An exemplary BSG protein sequence is depicted in SEQ ID NO:10. By "BSG" it is also meant herein polynucleotides which, due to degeneracy in genetic coding, comprise variations in nucleotide sequence as compared to SEQ ID NO: 1, 2, 3, 4, 5, 6, 7, 8 or 9, but which still encode the same protein. In the alternative, what is meant by BSG as used herein, means the native MRNA encoded by the gene comprising the polynucleotide sequence of SEQ ID NO: 1, 2, 3, 4, 5, 6, 7, 8 or 9, levels of the gene comprising the polynucleotide sequence of SEQ ID NO:. 1, 2, 3, 4, 5, 6, 7, 8 or 9, or levels of a polynucleotide which is capable of hybridizing under stringent conditions to the antisense sequence of SEQ ID NO: 1, 2, 3, 4, 5, 6, 7, 8 or 9. Such levels are preferably measured in at least one of, cells, tissues and/or bodily fluids, including determination of normal and abnormal levels. Thus, for instance, a diagnostic assay in accordance with the invention for measuring changes in levels of any one of the BSG proteins compared to normal control bodily fluids, cells, or tissue samples may be used to diagnose the presence of cancers, including breast cancer. By "change" it is meant either an increase or decrease in levels of the BSG. For example, for BSGs such as Mam001 (SEQ ID NO:2), Mam004 (SEQ ID NO:4/SEQ ID NO:10) and Mam005 (SEQ ID NO:3), an increase in levels as compared to normal human controls is associated with breast cancer, metastasis and progression of the cancer, while a decrease in levels is association with regression and/or remission. For the BSG Mam002 (SEQ ID NO:1), a decrease in levels as compared to normal human controls is associated with breast cancer, metastasis and progression while an increase is associated with regression and/or remission. Any of the 9 BSGs may be measured alone in the methods of the invention, or all together or any combination of the nine.

All the methods of the present invention may optionally include measuring the levels of other cancer markers as well as BSG. Other cancer markers, in addition to BSG, such as BRCA1 are known to those of skill in the art.

Diagnostic Assays

The present invention provides methods for diagnosing the presence of breast cancer by analyzing for changes in levels of BSG in cells, tissues or bodily fluids compared with levels of BSG in cells, tissues or bodily fluids of preferably the same type from a normal human control. As demonstrated herein an increase in levels of BSGs such as Mam001 (SEQ ID NO:2), Mam004 (SEQ ID NO:4/SEQ ID NO:10) or Mam005 (SEQ ID NO:3) in the patient versus the normal human control is associated with the presence of breast cancer, while a decrease in levels of BSGs such as Mam002 (SEQ ID NO:1) in the patient versus the normal human control is associated with the presence of breast cancer.

Without limiting the instant invention, typically, for a quantitative diagnostic assay a positive result indicating the patient being tested has cancer is one in which cells, tissues, or bodily fluid levels of the cancer marker, such as BSG, are at least two times higher or lower, and most preferably are at least five times higher or lower, than in preferably the same cells, tissues, or bodily fluid of a normal human control.

The present invention also provides a method of diagnosing metastatic breast cancer in a patient having breast cancer which has not yet metastasized for the onset of metastasis.

In the method of the present invention, a human cancer patient suspected of having breast cancer which may have metastasized (but which was not previously known to have metastasized) is identified. This is accomplished by a variety of means known to those of skill in the art. For example, in the case of breast cancer, patients are typically diagnosed with breast cancer following traditional detection methods.

In the present invention, determining the presence of BSG level in cells, tissues, or bodily fluid, is particularly useful for discriminating between breast cancer which has not metastasized and breast cancer which has metastasized. Existing techniques have difficulty discriminating between breast cancer which has metastasized and breast cancer which has not metastasized and proper treatment selection is often dependent upon such knowledge.

In the present invention, the cancer marker levels measured in such cells, tissues, or bodily fluid is BSG, and are compared with levels of BSG in preferably the same cells, tissue, or bodily fluid type of a normal human control. That is, if the cancer marker being observed is just BSG in serum, this level is preferably compared with the level of BSG in serum of a normal human patient. An increase in BSGs such as Mam001 (SEQ ID NO:2), Mam004 (SEQ ID NO:4/SEQ ID NO:10) or Mam005 (SEQ ID NO:3) in the patient versus the normal human control is associated with breast cancer which has metastasized while a decrease in BSGs such as Mam002 (SEQ ID NO:1) in the patient versus the normal human control is associated with breast cancer which has metastasized.

Without limiting the instant invention, typically, for a quantitative diagnostic assay a positive result indicating the cancer in the patient being tested or monitored has metastasized is one in which cells, tissues, or bodily fluid levels of the cancer marker, such as BSG, are at least two times higher or lower, and most preferably are at least five times higher or lower, than in preferably the same cells, tissues, or bodily fluid of a normal patient.

Normal human control as used herein includes a human patient without cancer and/or non cancerous samples from the patient; in the methods for diagnosing or monitoring for metastasis, normal human control preferably comprises samples from a human patient that is determined by reliable methods to have breast cancer which has not metastasized.

Staging

The invention also provides a method of staging breast cancer in a human patient. The method comprises identifying a human patient having such cancer; analyzing a sample of cells, tissues, or bodily fluid from such patient for BSG. Then, the method compares BSG levels in such cells, tissues, or bodily fluid with levels of BSG in preferably the same cells, tissues, or bodily fluid type of a normal human control sample, wherein an increase in levels of BSGs such as Mam001 (SEQ ID NO:2), Mam004 (SEQ ID NO:4/SEQ ID NO:10) or Mam005 (SEQ ID NO:3) or a decrease in levels of BSGs such as Mam002 (SEQ ID NO:1) in the patient versus the normal human control is associated with a cancer which is progressing and a decrease in levels of BSGs such as Mam001 (SEQ ID NO:2) Mam004 (SEQ ID NO:4/SEQ ID NO:10) or Mam005 (SEQ ID NO:3)(but generally still increased over true normal levels) or an increase in levels of BSGs such as Mam002 (SEQ ID NO:1) (but generally still decreased as compared to normal levels) is associated with a cancer which is regressing or in remission.

Monitoring

Further provided is a method of monitoring breast cancer in a human having such cancer for the onset of metastasis. The method comprises identifying a human patient having such cancer that is not known to have metastasized; periodically analyzing a sample of cells, tissues, or bodily fluid from such patient for BSG; comparing the BSG levels in such cells, tissue, or bodily fluid with levels of BSG in preferably the same cells, tissues, or bodily fluid type of a normal human control sample, wherein an increase in levels of BSGs such as Mam001 (SEQ ID NO:2), Mam004 (SEQ ID NO:4/SEQ ID NO:10) or Mam005 (SEQ ID NO:3) or a decrease in levels of BSGs such as Mam002 (SEQ ID NO:1) in the patient versus the normal human control is associated with a cancer which has metastasized. In this method, normal human control samples may also include prior patient samples.

Further provided by this invention is a method of monitoring the change in stage of breast cancer in a human having such cancer. The method comprises identifying a human patient having such cancer; periodically analyzing a sample of cells, tissues, or bodily fluid from such patient for BSG; comparing the BSG levels in such cells, tissue, or bodily fluid with levels of BSG in preferably the same cells, tissues, or bodily fluid type of a normal human control sample, wherein an increase in levels of BSGs such as Mam001 (SEQ ID NO:2), Mam004 (SEQ ID NO:4/SEQ ID NO:10) or Mam005 (SEQ ID NO:3) or a decrease in levels of BSGs such as Mam002 (SEQ ID NO:1) in the patient versus the normal human control is associated with a cancer which is progressing in stage and a decrease in the levels of BSGs such as Mam001 (SEQ ID NO:2), Mam004 (SEQ ID NO:4/SEQ ID NO:10) or Mam005 (SEQ ID NO:3) or an increase in levels of BSGs such as Mam002 (SEQ ID NO:1) is associated with a cancer which is regressing in stage or in remission.

Monitoring such patient for onset of metastasis is periodic and preferably done on a quarterly basis. However, this may be more or less frequent depending on the cancer, the particular patient, and the stage of the cancer.

Prognostic Testing and Clinical Trial Monitoring

The methods described herein can further be utilized as prognostic assays to identify subjects having or at risk of developing a disease or disorder associated with altered levels of BSG. The present invention provides a method in which a test sample is obtained from a human patient and BSG is detected. The presence of higher levels of Mam001 (SEQ ID NO:2), Mam004 (SEQ ID NO:4/SEQ ID NO:10) or Mam005 (SEQ ID NO:3) or lower levels of Mam002 (SEQ ID NO:1) as compared to normal human controls is diagnostic for the human patient being at risk for developing cancer, particularly breast cancer.

The effectiveness of therapeutic agents to alter expression or activity of the BSGs of the invention can also be monitored by analyzing levels of expression of the BSGs in a human patient in clinical trials or in in vitro screening assays such as in human cells. In this way, the gene expression pattern can serve as a marker, indicative of the physiological response of the human patient, or cells as the case may be, to the agent being tested.

Detection of Genetic Lesions or Mutations

The methods of the present invention can also be used to detect genetic lesions or mutations in BSG, thereby determining if a human with the genetic lesion is at risk for breast cancer or has breast cancer. Genetic lesions can be detected, for example, by ascertaining the existence of a deletion and/or addition and/or substitution of one or more nucleotides from the BSGs of this invention, a chromosomal rearrangement of BSG, aberrant modification of BSG (such as of the methylation pattern of the genomic DNA), the presence of a non-wild type splicing pattern of a mRNA transcript of BSG, allelic loss of BSG, and/or inappropriate post-translational modification of BSG protein. Methods to detect such lesions in a BSG of this invention are known to those of skill in the art.

Assay Techniques

Assay techniques that can be used to determine levels of gene expression, such as BSG of the present invention, in a sample derived from a host are well-known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to BSG, preferably a monoclonal antibody. In addition a reporter antibody generally is prepared which binds specifically to BSG. The reporter antibody is attached to a detectable reagent such as radioactive, fluorescent or enzymatic reagent, for example horseradish peroxidase enzyme or alkaline phosphatase.

To carry out the ELISA, antibody specific to BSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time BSG binds to the specific antibody attached to the polystyrene dish. Unbound sample is washed out with buffer. A reporter antibody specifically directed to BSG and linked to horseradish peroxidase is placed in the dish resulting in binding of the reporter antibody to any monoclonal antibody bound to BSG. Unattached reporter antibody is then washed out. Reagents for peroxidase activity, including a calorimetric substrate are then added to the dish. Immobilized peroxidase, linked to BSG antibodies, produces a colored reaction product. The amount of color developed in a given time period is proportional to the amount of BSG protein present in the sample. Quantitative results typically are obtained by reference to a standard curve.

A competition assay may be employed wherein antibodies specific to BSG attached to a solid support and labeled BSG and a sample derived from the host are passed over the solid support and the amount of label detected attached to the solid support can be correlated to a quantity of BSG in the sample.

Using all or a portion of a nucleic acid sequence of BSG of the present invention as a hybridization probe, nucleic acid methods can also be used to detect levels of BSG mRNA as a marker for breast cancer. Polymerase chain reaction (PCR) and other nucleic acid methods, such as ligase chain reaction (LCR) and nucleic acid sequence based amplification (NASBA), can be used to detect cells for diagnosis and monitoring of various malignancies. For example, reverse-transcriptase PCR (RT-PCR) is a powerful technique which can be used to detect the presence of a specific MRNA population in a complex mixture of thousands of other mRNA species. In RT-PCR, an MRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the MRNA is highly specific for the cell that produces it, RT-PCR can be used to identify the presence and/or absence of a specific type of cell.

Hybridization to clones or oligonucleotides arrayed on a solid support (i.e. gridding) can be used to both detect the expression of and quantitate the level of expression of that gene. In this approach, all or a portion of a cDNA encoding the BSG is fixed to a substrate. The substrate may be of any suitable type including, but not limited to, glass, nitrocellulose, nylon or plastic. At least a portion of the DNA encoding the BSG is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including, but not limited to, radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those skilled in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood.

In Vivo Targeting of BSG/Breast Cancer Therapy

Identification of BSGs is also useful in the rational design of new therapeutics for imaging and treating cancers, and in particular breast cancer. For example, in one embodiment, antibodies which specifically bind to BSG can be raised and used in vivo in patients suspected of suffering from breast cancer. Antibodies which specifically bind BSG can be injected into a patient suspected of having breast cancer for diagnostic and/or therapeutic purposes. Thus, another aspect of the present invention provides for a method for preventing the onset and treatment of breast cancer in a human patient in need of such treatment by administering to the patient an effective amount of antibody. By "effective amount" it is meant the amount or concentration of antibody needed to bind to the target antigens expressed on the tumor to cause tumor shrinkage for surgical removal, or disappearance of the tumor. The binding of the antibody to an overexpressed BSG is believed to cause the death of the cancer cell expressing such BSG. The preparation and use of antibodies for in vivo diagnosis and treatment is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against a BSG can be used in a similar manner. Labeled antibodies which specifically bind BSGs can be injected into patients suspected of having breast cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Presence of the label, as compared to imaging of normal tissue, permits determination of the spread of the cancer. The amount of label within an organ or tissue also allows determination of the presence or absence of cancer in that organ or tissue.

Antibodies which can be used in in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Screening Assays

The present invention also provides methods for identifying modulators which bind to BSG protein or have a modulatory effect on the expression or activity of BSG protein. Modulators which decrease the expression or activity of BSG proteins such as Mam001 (SEQ ID NO:2), Mam004 (SEQ ID NO:4/SEQ ID NO:10) and Mam005 (SEQ ID NO:3) or increase the expression or activity of the BSG Mam002 (SEQ ID NO:1) are believed to be useful in treating breast cancer. Such screening assays are known to those of skill in the art and include, without limitation, cell-based assays and cell free assays.

Small molecules predicted via computer imaging to specifically bind to regions of BSG can also be designed, synthesized and tested for use in the imaging and treatment of breast cancer. Further, libraries of molecules can be screened for potential anticancer agents by assessing the ability of the molecule to bind to the BSGs identified herein. Molecules identified in the library as being capable of binding to BSG are key candidates for further evaluation for use in the treatment of breast cancer. In a preferred embodiment, these molecules will downregulate expression and/or activity of BSGs such as Mam001 (SEQ ID NO:2), Mam004 (SEQ ID NO:4/SEQ ID NO:10) and Mam005 (SEQ ID NO:3) and/or upregulate expression and/or activity of the BSG Mam002 (SEQ ID NO:1) in cells.

Adoptive Immunotherapy and Vaccines

Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category and investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg, S. A., et al., 1988, N. England J. Med. 319:1676–1680).

The present invention relates to compositions and methods of adoptive immunotherapy for the prevention and/or treatment of primary and metastatic breast cancer in humans using macrophages sensitized to the antigenic BSG molecules, with or without non-covalent complexes of heat shock protein (hsp). Antigenicity or immunogenicity of the BSG is readily confirmed by the ability of the BSG protein or a fragment thereof to raise antibodies or educate naive effector cells, which in turn lyse target cells expressing the antigen (or epitope).

Cancer cells are, by definition, abnormal and contain proteins which should be recognized by the immune system as foreign since they are not present in normal tissues. However, the immune system often seems to ignore this abnormality and fails to attack tumors. The foreign BSG proteins that are produced by the cancer cells can be used to reveal their presence. The BSG is broken into short fragments, called tumor antigens, which are displayed on the surface of the cell. These tumor antigens are held or presented on the cell surface by molecules called MHC, of which there are two types: class I and II. Tumor antigens in association with MHC class I molecules are recognized by cytotoxic T cells while antigen-MHC class II complexes are recognized by a second subset of T cells called helper cells. These cells secrete cytokines which slow or stop tumor growth and help another type of white blood cell, B cells, to make antibodies against the tumor cells.

In adoptive immunotherapy, T cells or other antigen presenting cells (APCS) are stimulated outside the body (ex vivo), using the tumor specific BSG antigen. The stimulated cells are then reinfused into the patient where they attack the cancerous cells. Research has shown that using both cytotoxic and helper T cells is far more effective than using either subset alone. Additionally, the BSG antigen may be complexed with heat shock proteins to stimulate the APCs as described in U.S. Pat. No. 5,985,270.

The APCs can be selected from among those antigen presenting cells known in the art including, but not limited to, macrophages, dendritic cells, B lymphocytes, and a combination thereof, and are preferably macrophages. In a preferred use, wherein cells are autologous to the individual, autologous immune cells such as lymphocytes, macrophages or other APCs are used to circumvent the issue of whom to select as the donor of the immune cells for adoptive transfer. Another problem circumvented by use of autologous immune cells is graft versus host disease which can be fatal if unsuccessfully treated.

In adoptive immunotherapy with gene therapy, DNA of the BSG can be introduced into effector cells similarly as in conventional gene therapy. This can enhance the cytotoxicity of the effector cells to tumor cells as they have been manipulated to produce the antigenic protein resulting in improvement of the adoptive immunotherapy.

BSG antigens of this invention are also useful as components of breast cancer vaccines. The vaccine comprises an immunogenically stimulatory amount of a BSG antigen. Immunogenically stimulatory amount refers to that amount of antigen that is able to invoke the desired immune response in the recipient for the amelioration, or treatment of breast cancer. Effective amounts may be determined empirically by standard procedures well known to those skilled in the art.

The BSG antigen may be provided in any one of a number of vaccine formulations which are designed to induce the desired type of immune response, e.g., antibody and/or cell mediated. Such formulations are known in the art and include, but are not limited to, formulations such as those described in U.S. Pat. No. 5,585,103. Vaccine formulations of the present invention used to stimulate immune responses can also include pharmaceutically acceptable adjuvants.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Example 1

Identification of BSGs were carried out by a systematic analysis of data in the LIFESEQ database available from Incyte Pharmaceuticals, Palo Alto, Calif., using the data mining Cancer Leads Automatic Search Package (CLASP) developed by diaDexus LLC, Santa Clara, Calif.

The CLASP performs the following steps:

Selection of highly expressed organ specific genes based on the abundance level of the corresponding EST in the targeted organ versus all the other organs.

Analysis of the expression level of each highly expressed organ specific genes in normal, tumor tissue, disease tissue and tissue libraries associated with tumor or disease.

Selection of the candidates demonstrating component ESTs were exclusively or more frequently found in tumor libraries.

CLASP allows the identification of highly expressed organ and cancer specific genes useful in the diagnosis of breast cancer.

TABLE 1

| | BSGs Sequences | |
|---|---|---|
| SEQ ID NO: | LS Clone ID | LSA Gene ID |
| 1 | 2740238 (Mam002) | 242151 |
| 2 | 1730886 (Mam001) | 238469 |
| 3 | y155b03 (Mam005) | 348845 |
| 4 | 2613064 (Mam004) | 27052 |
| 5 | 894184 | 221086 |
| 6 | 2299454 | 27681 |

TABLE 1-continued

| | BSGs Sequences | |
|---|---|---|
| SEQ ID NO: | LS Clone ID | LSA Gene ID |
| 7 | 2258254 | 248176 |
| 8 | 789767 | 156580 |
| 9 | 1213903 | 219737 |

The following example was carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 2
Relative Quantitation of Gene Expression

Real-time quantitative PCR with fluorescent Taqman probes is a quantitative detection system utilizing the 5'-3' nuclease activity of Taq DNA polymerase. The method uses an internal fluorescent oligonucleotide probe. (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster.City, Calif., USA).

Amplification of an endogenous control was used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) was used as this endogenous control. To calculate relative Quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System). To evaluate the tissue distribution, and the level of breast specific markers (BSM) Mam001 (SEQ ID NO:2), Mam002 (SEQ ID NO:1), Mam004 (SEQ ID NO:4/SEQ ID NO:10) and Mam005 (SEQ ID NO:3) in normal and cancer tissue, total RNA was extracted from cancer and matched normal adjacent tissues (NAT) and from unmatched cancer and normal tissues. Subsequently, first strand cDNA was prepared with reverse transcriptase and the polymerase chain reaction carried out using primers and Taqman probes specific to each of Mam001 (SEQ ID NO:2), Mam002 (SEQ ID NO:1), Mam004 (SEQ ID NO:4/SEQ ID NO:10) and Mam005 (SEQ ID NO:3) respectively. The results are obtained using the ABI PRISM 7700 Sequence Detector. The numbers are relative levels of expression of Mam001 (SEQ ID NO:2), Mam002 (SEQ ID NO:1), Mam004 (SEQ ID NO:4/SEQ ID NO:10) and Mam005 (SEQ ID NO:3) compared to their respective calibrators.
Measurement of SEQ ID NO:2; Clone ID:1730886; Gene ID: 238469 (Mam001)

The numbers depicted in Table 2 are relative levels of expression in 12 normal tissues of Mam001 (SEQ ID NO:2) compared to testis (calibrator). These RNA samples were obtained commercially and were generated by pooling samples from a particular tissue from different individuals.

TABLE 2

Relative levels of Mam001 (SEQ ID NO:2) Expression in Pooled Samples

| Tissue | NORMAL |
| --- | --- |
| Brain | 0 |
| Heart | 0 |
| Kidney | 0 |
| Liver | 0 |
| Lung | 0 |
| Mammary | 6 |
| Prostate | 0 |
| Muscle | 0 |
| Small Intestine | 0 |
| Testis | 1 |
| Thymus | 0 |
| Uterus | 0 |

The relative levels of expression in Table 2 show that Mam001 (SEQ ID NO:2) mRNA expression is detected in the pool of normal mammary and in testis but not in the other 10 normal tissue pools analyzed. These results demonstrate that Mam001 (SEQ ID NO:2) mRNA expression is highly specific for mammary tissue and is also found in testis. Expression in a male specific tissue is not relevant in detecting cancer in female specific tissues The tissues shown in Table 2 are pooled samples from different individuals. The tissues shown in Table 3 were obtained from individuals and are not pooled. Hence the values for mRNA expression levels shown in Table 2 cannot be directly compared to the values shown in Table 3.

The numbers depicted in Table 3 are relative levels of expression of Mam001 (SEQ ID NO:2) compared to testis (calibrator), in 24 pairs of matching samples. Each matching pair contains the cancer sample for a particular tissue and the normal adjacent tissue (NAT) sample for that same tissue from the same individual.

TABLE 3

Relative levels of Mam001 (SEQ ID NO:2) Expression in Individual Samples

| Sample ID | Tissue | Cancer | Matching Normal |
| --- | --- | --- | --- |
| Mam 47XP | Mammary Gland | 0 | 0 |
| Mam A06X | Mammary Gland | 23 | 1 |
| Mam B011X | Mammary Gland | 0 | 5 |
| Mam 603X/C034 | Mammary Gland | 0 | 2.10 |
| Mam 162X | Mammary Gland | 1.96 | 0.15 |
| Mam 42DN | Mammary Gland | 0.38 | 1.27 |
| Mam S079 | Mammary Gland | 0.34 | 0.36 |
| Mam S123 | Mammary Gland | 0.03 | 0.87 |
| Mam S516 | Mammary Gland | 0.43 | 0.53 |
| Mam S699 | Mammary Gland | 0.40 | 0.66 |
| Mam S997 | Mammary Gland | 0.41 | 0.51 |
| Sto AC44 | Stomach | 0 | 0 |
| TST 39X | Testis | 0 | 0 |
| Cln SG45 | Colon | a | 0 |
| Cln TX01 | Colon | 0 | 0 |
| Cvx NK23 | Cervix | 0 | 0 |
| Cvx NK24 | Cervix | 0 | 0 |
| Endo 3AX | Endometrium | 0 | 0 |
| Endo 4XA | Endometrium | 0 | 0 |
| Endo 5XA | Endometrium | 0 | 0 |
| Kid 11XD | Kidney | 0 | 0 |
| Kid 5XD | Kidney | 0 | 0 |
| Lng C20X | Lung | 0 | 0 |
| Lng SQ56 | Lung | 0 | 0 |

Among 48 samples in Table 3 representing 8 different tissues expression is seen only in mammary tissues. These results confirm the tissue specificity results obtained with normal samples shown in Table 2. Table 2 and Table 3 represent a combined total of 60 samples in 16 human tissue types. Thirty-six samples representing 14 different tissue types excluding breast and testis had no detected Mam001 (SEQ ID NO:2) mRNA (Table 2 and 3). Other than breast tissue, Mam001 (SEQ ID NO:2) is detected only in one other tissue type (Testis) and then only in the pooled tissue sample (Table 2) but not in the matched testis cancer samples (Table 3).

Comparisons of the level of mRNA expression in breast cancer samples and the normal adjacent tissue from the same individuals are shown in Table 3. Mam001 (SEQ ID NO:2) is expressed at higher levels in 2 of 11 breast cancer tissues (Mam A06X and Mam 162X) compared with the corresponding normal adjacent tissue. The level of Mam001 (SEQ ID NO:2) expression is lower in breast cancer compared to normal adjacent tissue in four matched samples (Mam B011X, Mam 603X/CO34, Mam 42DN and Mam S123). No expression was detected in one set of matched samples (Mam 47XP). Equivalent levels or very similar levels of expression were detected in four other matched samples (Mam S079, Mam S516, Mam S699 and Mam S997). However increasing cancer mass might in these cases result in an overall increase in the total amount of expression.

The high level of tissue specificity and increased or equivalent expression in 6 of 11 individuals is demonstrative of Mam001 (SEQ ID NO:2) being a diagnostic marker for detection of mammary cancer cells using mRNA.

Measurement of SEQ ID NO:1; Clone ID: 2740238; Gene ID 242151 (Mam002)

The numbers depicted in Table 5 are relative levels of expression in 12 normal tissues of Mam002 (SEQ ID NO:1) compared to Thymus (calibrator). These RNA samples were obtained commercially and were generated by pooling samples from a particular tissue from different individuals.

TABLE 4

Relative levels of Mam002 (SEQ ID NO:1) Expression in Pooled Samples

| Tissue | NORMAL |
| --- | --- |
| Brain | 0.03 |
| Heart | 0.01 |
| Kidney | 0 |
| Liver | 0 |
| Lung | 0.06 |
| Mammary | 289.01 |
| Muscle | 0 |
| Prostate | 0.31 |
| Small Int. | 0 |
| Testis | 0.08 |
| Thymus | 1.00 |
| Uterus | 0 |

The relative levels of expression in Table 4 show that Mam002 (SEQ ID NO:1) mRNA expression is detected at a high level in the pool of normal mammary but at very low levels in the other 11 normal tissue pools analyzed. These results demonstrate that Mam002 (SEQ ID NO:1) MRNA expression is highly specific for mammary tissue.

The tissues shown in Table 4 are pooled samples from different individuals. The tissues shown in Table 5 were obtained from individuals and are not pooled. Hence the values for mRNA expression levels shown in Table 4 cannot be directly compared to the values shown in Table 5.

The numbers depicted in Table 5 are relative levels of expression of Mam002 (SEQ ID NO:1) compared to thymus (calibrator) in 27 pairs of matching samples. Each matching pair contains the cancer sample for a particular tissue and the normal adjacent tissue (NAT) sample for that same tissue from the same individual. In addition 2 unmatched mammary samples from normal tissues and one unmatched ovarian cancer and one normal (non-cancerous) ovary were also tested.

TABLE 5

Relative levels of Mam002 (SEQ ID NO:1) Expression in Individual Samples

| Sample ID | Tissue | Cancer | Matching | Normal |
|---|---|---|---|---|
| Mam 12X | Mammary Gland | 7.2 | 69 | |
| Mam 42DN | Mammary Gland | 1051 | 2075 | |
| Mam 59X | Mammary Gland | 7.0 | 15.5 | |
| Mam A06X | Mammary Gland | 1655 | 1781 | |
| Mam B011X | Mammary Gland | 32.1 | 2311 | |
| Mam S127 | Mammary Gland | 1.73 | 0 | |
| Mam S516 | Mammary Gland | 9.72 | 69.95 | |
| Mam S699 | Mammary Gland | 83.46 | 75.65 | |
| Mam S854 | Mammary Gland | 133.23 | 836.56 | |
| Mam S967 | Mammary Gland | 59.77 | 188.28 | |
| Mam S997 | Mammary Gland | 94.14 | 73.64 | |
| Mam 162X | Mammary Gland | 674.0 | 31.1 | |
| Mam C012 | Mammary Gland | N/A | N/A | 11379.3 |
| Mam C034 | Mammary Gland | N/A | N/A | 3502.6 |
| Mam S079 | Mammary Gland | 11772.5 | 903.5 | |
| Mam S123 | Mammary Gland | 3.4 | 170.5 | |
| Ovr 103X | Ovary | 0 | 0 | |
| Ovr 1118 | Ovary | 0.13 | N/A | |
| Ovr 35GA | Ovary | N/A | N/A | 0.13 |
| Utr 23XU | Uterus | 5.6 | 0 | |
| Utr 135X0 | Uterus | 0 | 0 | |
| Cvx NK24 | Cervix | 0.9 | 1.4 | |
| End 4XA | Endometrium | 32.2 | 0 | |
| Cln AS43 | Colon | 2.3 | 0 | |
| Cln AS45 | Colon | 0 | 0 | |
| Cln RC01 | Colon | 0.2 | 0 | |
| Lng AC90 | Lung | 0 | 2.0 | |
| Lng LC109 | Lung | 0 | 0.6 | |
| Lng SC32 | Lung | 0.8 | 0 | |
| Sto AC93 | Stomach | 0 | 0 | |
| Tst 39X | Testis | 1.97 | 0 | |

Among 58 samples in Table 5 representing 9 different tissues, the highest expression is seen in mammary tissues. Amongst the non-breast tissues which show expression, only one sample (End 4XA) has expression comparable to that seen in the majority of the breast samples tested. This sample is endometrial tissue, which is a female specific tissue. These results confirm the tissue specificity results obtained with normal samples shown in Table 4. Table 4 and Table 5 represent a combined total of 70 samples in 17 human tissue types. Twenty-two samples representing 11 different tissue types excluding breast had no detected Mam002 (SEQ ID NO:1) mRNA (Table 4 and Table 5).

Comparisons of the level of mRNA expression in breast cancer samples and the normal adjacent tissue from the same individuals are shown in Table 5. Mam002 (SEQ ID NO:1) is expressed at higher levels in 3 of 13 matched breast cancer tissues (Samples Mam S127, Mam 162X and Mam S079) compared with the corresponding normal adjacent tissue. The level of Mam002 (SEQ ID NO:1) expression is lower in breast cancer compared to normal adjacent tissue in eight individuals (Mam 12X, Mam 42DN, Mam 59X, Mam B011X, Mam S516, Mam S854, Mam S967, and Mam S123). Equivalent levels or very similar levels of expression were detected in three other matched samples (Samples Mam A06X, Mam S699 and Mam S997).

The high level of tissue specificity is demonstrative of Mam002 (SEQ ID NO:1) being a diagnostic marker for detection of mammary cancer cells using mRNA. Breast tissue is the only significant source of this gene's expression so far detected. Eight of 13 matched samples have lower levels of expression in cancer than normal adjacent tissue. Thus, decreased expression of this gene appears to be diagnostic of cancer presence.

Measurement of SEQ ID NO:4; Clone ID: 2613064; Gene ID: 27052 (Mam004)

The numbers depicted in Table 6 are relative levels of expression in 12 normal tissues of Mam004 (SEQ ID NO:4) compared to mammary (calibrator). These RNA samples were obtained commercially and were generated by pooling samples from a particular tissue from different individuals.

TABLE 6

Relative levels of Mam004 (SEQ ID NO:4) Expression in Pooled Samples

| Tissue | NORMAL |
|---|---|
| Brain | 0.059 |
| Heart | 0.131 |
| Kidney | 0.018 |
| Liver | 0 |
| Lung | 0.478 |
| Mammary | 1.000 |
| Prostate | 0.459 |
| Muscle | 0.003 |
| Small Intestine | 0.048 |
| Testis | 0.130 |
| Thymus | 0.030 |
| Uterus | 0.071 |

The relative levels of expression in Table 6 show that Mam004 (SEQ ID NO:4) mRNA expression is detected in the pool of normal mammary and also in other tissues including lung, prostate, testis and heart. These results demonstrate that although more highly expressed in normal breast tissue Mam004(SEQ ID NO:4) MRNA expression is not specific for mammary gland.

The tissues shown in Table 6 are pooled samples from different individuals. The tissues shown in Table 7 were obtained from individuals and are not pooled. Hence the values for mRNA expression levels shown in Table 6 cannot be directly compared to the values shown in Table 7.

The numbers depicted in Table 7 are relative levels of expression of Mam004 (SEQ ID NO:4) compared to mammary (calibrator), in 23 pairs of matching samples. Each matching pair contains the cancer sample for a particular tissue and the normal adjacent tissue (NAT) sample for that same tissue from the same individual.

TABLE 7

Relative levels of Mam004 (SEQ ID NO:4) Expression in Individual Samples

| Sample ID | Tissue | Cancer | Matching |
|---|---|---|---|
| Mam 12B | Mammary Gland | 0 | 0 |
| Mam 12X | Mammary Gland | 13.454 | 0 |
| Mam 603X | Mammary Gland | 30.484 | 0 |
| Mam 59X | Mammary Gland | 1.306 | 0 |
| Mam 162X | Mammary Gland | 0.71 | 0.04 |
| Mam 42DN | Mammary Gland | 0.25 | 2.17 |
| Mam S079 | Mammary Gland | 42.18 | 0.47 |
| Mam S123 | Mammary Gland | 0.01 | 0 |
| Mam S516 | Mammary Gland | 1.17 | 0.41 |
| Mam S699 | Mammary Gland | 0.11 | 0.55 |
| Mam S997 | Mammary Gland | 10.43 | 1.29 |
| Sto AC44 | Stomach | 0.61 | 0 |
| Cln 5G45 | Colon | 0.04 | 0 |
| Cln TX01 | Colon | 0 | 0 |
| Cvx NK23 | Cervix | 0 | 0 |
| Cvx NK24 | Cervix | 0 | 0 |
| Endo 3Ax | Endometrium | 0 | 0 |
| Endo 4XA | Endometrium | 0 | 0 |
| Endo 5XA | Endometrium | 0 | 2.73 |
| Kid 11XD | Kidney | 0 | 0 |
| Kid 5XD | Kidney | 0 | 2.63 |
| Lng C20X | Lung | 0 | 0 |
| Lng SQ56 | Lung | 10.37 | 0 |

Among 46 samples in Table 7 representing 7 different tissues expression is highest in breast tissues particularly cancers. Expression comparable to that seen in breast samples is also seen in 1 of 4 lung samples (Sample 23), 1 of 4 kidney samples (Sample 21) and 1 of 6 endometrial samples (Sample 19). Table 6 and Table 7 represent a combined total of 58 samples in 16 human tissue types. Twenty samples representing 7 different tissue types excluding breast had no detected Mam004 (SEQ ID NO:4) mRNA (Table 6 and Table 7).

Comparisons of the level of mRNA expression in breast cancer samples and the normal adjacent tissue from the same individuals are shown in Table 7. Mam004 (SEQ ID NO:4) is expressed at higher levels in 8 of 11 breast cancer tissues (Mam 12X, Mam 603X, Mam 59X, Mam 162X, Mam S079, Mam S123, Mam S516 and Mam S997) compared with the corresponding normal adjacent tissue. The level of Mam004 (SEQ ID NO:4) expression is lower in breast cancer compared to normal adjacent tissue in two matched samples (Mam 42DN and Mam S699). No expression was detected in one matched sample (Mam 12B).

Elevated expression in the majority of matched cancer samples compared to normal adjacent tissue is indicative of Mam004 (SEQ ID NO:4) being a diagnostic marker for detection of mammary cancer cells using mRNA.

Measurement of SEQ ID NO:3; Clone ID:yl55b03; Gene ID: 348845 (Mam005)

The numbers depicted in Table 8 are relative levels of expression in 12 normal tissues of Mam005 (SEQ ID NO:3) compared to testis (calibrator). These RNA samples were obtained commercially and were generated by pooling samples from a particular tissue from different individuals.

Table 8

Relative levels of Mam005 (SEQ ID NO:3) Expression in Pooled Samples

| Tissue | NORMAL |
|---|---|
| Brain | 0 |
| Heart | 0.0002 |
| Kidney | 0.0001 |
| Liver | 0 |
| Lung | 0 |
| Mammary | 5.4076 |
| Muscle | 0 |
| Prostate | 0 |
| Small Intestine | 0 |
| Testis | 1 |
| Thymus | 0 |
| Uterus | 0 |

The relative levels of expression in Table 8 show that Mam005 (SEQ ID NO:3) mRNA expression is detected in the pool of normal mammary and in testis but is not present at significant levels in the other 10 normal tissue pools analyzed. These results demonstrate that Mam005 (SEQ ID NO:3) mRNA expression is highly specific for mammary tissue and is also found in testis. Expression in a male specific tissue is not relevant in detecting cancer in female specific tissues.

The tissues shown in Table 8 are pooled samples from different individuals. The tissues shown in Table 9 were obtained from individuals and are riot pooled. Hence the values for mRNA expression levels shown in Table 8 cannot be directly compared to the values shown in Table 9.

The numbers depicted in Table 9 are relative levels of expression of Mam005 (SEQ ID NO:3) compared to testis (calibrator), in 46 pairs of matching samples. Each matching pair contains the cancer sample for a particular tissue and the normal adjacent tissue sample for that same tissue from the same individual. In addition 2 unmatched mammary samples from normal tissues and one unmatched ovarian cancer and one normal (non-cancerous) ovary were also tested.

TABLE 9

Relative level of Mam005 (SEQ ID NO:3) Expression in Individual Samples

| Sample ID | Tissue | Cancer | Matching | Normal |
|---|---|---|---|---|
| Mam 12X | Mammary Gland | 0.33 | 0.71 | |
| Mam 42DN | Mammary Gland | 0.22 | 0.63 | |
| Mam 59X | Mammary Gland | 0.03 | 0.23 | |
| Mam A06X | Mammary Gland | 70.77 | 0.56 | |
| Mam B011X | Mammary Gland | 0.03 | 1.52 | |
| Mam 162X | Mammary Gland | 0.43 | 0.09 | |
| Mam C012 | Mammary Gland | N/A | N/A | 1.6 |
| Mam C034 | Mammary Gland | N/A | N/A | 2.9 |
| Mam S079 | Mammary Gland | 0.22 | 0.13 | |
| Mam S123 | Mammary Gland | 0.01 | 0.23 | |
| Mam S127 | Mammary Gland | 0 | 0.28 | |

TABLE 9-continued

Relative level of Mam005 (SEQ ID NO:3) Expression in Individual Samples

| Sample ID | Tissue | Cancer | Matching | Normal |
|---|---|---|---|---|
| Mam S516 | Mammary Gland | 0.15 | 0.05 | |
| Mam S699 | Mammary Gland | 0.21 | 0.42 | |
| Mam S854 | Mammary Gland | 1.12 | 0.54 | |
| Mam S967 | Mammary Gland | 30.61 | 0.54 | |
| Mam S997 | Mammary Gland | 0.40 | 0.22 | |
| Mam 14DN | Mammary Gland | 0.07 | 0 | |
| Mam 699F | Mammary Gland | 0.01 | 0.09 | |
| Mam S621 | Mammary Gland | 1.82 | 0 | |
| Mam S918 | Mammary Gland | 6.89 | 1.06 | |
| Cln CM67 | Colon | 0 | 0 | |
| Cln DC19 | Colon | 0 | 0 | |
| Cln AS43 | Colon | 0 | 0 | |
| Cln AS45 | Colon | 0 | 0 | |
| Cln RC01 | Colon | 0.0012 | 0.0003 | |
| Lng AC90 | Lung | 0 | 0 | |
| Lng LC109 | Lung | 0 | 0 | |
| Lng SQ32 | Lung | 0 | 0 | |
| Lng SQ43 | Lung | 0 | 0 | |
| Ovr 103X | Ovary | 0 | 0 | |
| Ovr 1118 | Ovary | 0 | N/A | |
| Ovr A084 | Ovary | 0 | 0 | |
| Ovr G021 | Ovary | 0 | 0 | |
| Ovr 35GA | Ovary | N/A | N/A | 0 |
| Cvx NK23 | Cervix | 0 | 0 | |
| Cvx NK24 | Cervix | 0 | 0 | |
| Endo 3AX | Endometrium | 0 | 0 | |
| Endo 4XA | Endometrium | 0 | 0 | |
| Sto 758S | Stomach | 0 | 0 | |
| Sto AC44 | Stomach | 0 | 0 | |
| Sto AC93 | Stomach | 0 | 0 | |
| Tst 39X | Testis | 0.01 | 0.01 | |
| Utr 85XU | Uterus | 0 | 0 | |
| Utr 135X0 | Uterus | 0 | 0 | |
| Utr 23XU | Uterus | 0 | 0 | |
| Kid 124D | Kidney | 0 | 0 | |
| Lvr 15XA | Liver | 0 | 0 | |
| Pan C044 | Pancreas | 0 | 0 | |
| Skn 448S | Skin | 0 | 0 | |
| SmInt 21XA | Small Intestines | 0 | 0 | |

Among 96 samples in Table 9 representing 14 different tissues significant expression is seen only in breast tissues. These results confirm the tissue specificity results obtained with normal samples shown in Table 8. Table 8 and Table 9 represent a combined total of 108 samples in 18 human tissue types. Sixty-seven samples representing 16 different tissue types excluding breast and testis had either no or very low levels of detected Mam005 (SEQ ID NO:3) mRNA (Table 8 and Table 9).

Comparisons of the level of mRNA expression in breast cancer samples and the normal adjacent tissue from the same individuals are shown in Table 9. Mam005 (SEQ ID NO:3) is expressed at higher levels in 10 of 18 cancer and normal adjacent tissue samples (Mam A06X, Mam 162X, Mam S079, Mam S516, Mam S854, Mam S967, Mam S997, Mam 14DN, Mam S621, and Mam S918) compared with the corresponding normal adjacent tissue. The level of Mam005 (SEQ ID NO:3) expression is lower in breast cancer compared to normal adjacent tissue in eight cancer and normal adjacent tissue samples (Mam 12X, Mam 42DN, Mam 59X, Mam B011X, Mam S123, Mam S127, Mam S699 and Mam 699F). No expression was detected in two matching samples.

The high level of tissue specificity and overexpression in 10 of 18 matched cancer and normal adjacent tissue samples is indicative of Mam005 (SEQ ID NO:3) being a diagnostic marker for detection of mammary cancer cells using mRNA.

What is claimed is:

1. A method for diagnosing the presence of breast cancer in a patient comprising:
   (a) measuring levels of a breast specific gene (BSG) in cells, tissues or bodily fluids in said patient; and
   (b) comparing measured levels of BSG with levels of BSG in cells, tissues or bodily fluids from a normal human control,
   wherein said BSG comprises SEQ ID NO 1, 2, 3, 4, 5, 6, 7, 8 or 9, a protein encoded thereby, or a polynucleotide which, due to degeneracy in genetic coding, comprises variations in nucleotide sequence as compared to SEQ ID NO: 1, 2, 3, 4, 5, 6, 7, 8 or 9, but which still encodes the same protein as SEQ ID NO: 1, 2, 3, 4, 5, 6, 7, 8 or 9, and
   wherein a change in measured levels of BSG in the patient versus normal human control is associated with the presence of breast cancer.

2. A method of diagnosing metastatic breast cancer in a patient having breast cancer comprising:
   (a) identifying a patient having breast cancer that is not known to have metastasized;
   (b) measuring levels of a breast specific gene (BSG) in a sample of cells, tissues, or bodily fluid from said patient; and
   (c) comparing the measured BSG levels with levels of BSG in cells, tissue, or bodily fluid type of a normal human control,
   wherein said BSG comprises SEQ ID NO 1, 2, 3, 4, 5, 6, 7, 8 or 9, a protein encoded thereby, or a polynucleotide which, due to degeneracy in genetic coding, comprises variations in nucleotide sequence as compared to SEQ ID NO: 1, 2, 3, 4, 5, 6, 7, 8 or 9, but which still encodes the same protein as SEQ NO: 1, 2, 3, 4, 5, 6, 7, 8 or 9, and
   wherein a change in measured BSG levels in the patient versus the normal human control is associated with a cancer which has metastasized.

3. A method of staging breast cancer in a patient comprising:
   (a) identifying a patient having breast cancer;
   (b) measuring levels of a breast specific gene (BSG) in a sample of cells, tissues, or bodily fluid from said patient for BSG; and
   (c) comparing measured BSG levels with levels of BSG in cells, tissues, or bodily fluid type of a normal human control sample,
   wherein said BSG comprises SEQ ID NO 1, 2, 3, 4, 5, 6, 7, 8 or 9, a protein encoded thereby, or a polynucleotide which, due to degeneracy in genetic coding, comprises variations in nucleotide sequence as compared to SEQ ID NO: 1, 2, 3, 4, 5, 6, 7, 8 or 9, but which still encodes the same protein as SEQ ID NO: 1, 2, 3, 4, 5, 6, 7, 8 or 9, and
   wherein a change in measured BSG levels in said patient versus the normal human control is associated with a cancer which is progressing or regressing or in remission.

4. A method of monitoring breast cancer in a patient, having breast cancer for the onset of metastasis comprising:
   (a) identifying a patient having breast cancer that is not known to have metastasized;
   (b) periodically measuring breast specific gene (BSG) levels in a sample of cells, tissues, or bodily fluid from said patient; and
   (c) comparing the measured BSG levels with levels of BSG in cells, tissues, or bodily fluid type of a normal human control, wherein said BSG comprises SEQ ID NO 1, 2, 3, 4, 5, 6, 7, 8 or 9, a protein encoded thereby, or a polynucleotide which, due to degeneracy in genetic coding, comprises variations in nucleotide sequence as compared to SEQ ID NO: 1, 2, 3, 4, 5, 6, 7, 8 or 9, but which still encodes the same protein as SEQ ID NO: 1, 2, 3, 4, 5, 6, 7, 8 or 9 and wherein a change in BSG levels in the patient versus the normal human control is associated with a cancer which has metastasized.

5. A method of monitoring the change in stage of breast cancer in a patient having breast cancer comprising:
(a) identifying a patient having breast cancer;
(b) periodically measuring breast specific gene (BSG) levels in a sample of cells, tissues, or bodily fluid from said patient; and
(c) comparing the measured BSG levels with levels of BSG in cells, tissues, or bodily fluid type of a normal human control,
wherein said BSG comprises SEQ ID NO 1, 2, 3, 4, 5, 6, 7, 8 or 9, a protein encoded thereby, or a polynucleotide which, due to degeneracy in genetic coding, comprises variations in nucleotide sequence as compared to SEQ ID NO: 1, 2, 3, 4, 5, 6, 7, 8 or 9, but which still encodes the same protein as SEQ ID NO: 1, 2, 3, 4, 5, 6, 7, 8 or 9, and
wherein a change in measured BSG levels in the patient versus the normal human control is associated with a cancer which is progressing in stage, which is regressing in stage, or in remission.

6. The method of claim 1, 2, 3, 4 or 5 wherein the change associated with the presence, metastasis or progression of breast cancer in said patient is an increase in measured BSG levels in the patient and the BSG comprises Mam001 (SEQ ID NO:2), Mam004 (SEQ ID NO:4 or SEQ ID NO:10) or Mam005 (SEQ ID NO:3).

7. The method of claim 1, 2, 3, 4 or 5 wherein the change associated with the presence, metastasis or progression of breast cancer in said patient is a decrease in measured BSG levels in the patient and the BSG comprises Mam002 (SEQ ID NO:1).

8. The method of claim 3 or 5 wherein the change associated with the regression or remission of breast cancer in said patient is a decrease in measured BSG levels in the patient and the BSG comprises Mam001 (SEQ ID NO:2), Mam004 (SEQ ID NO:4 or SEQ ID NO:10) or Mam005 (SEQ ID NO:3).

9. The method of claim 3 or 5 wherein the change associated with the regression or remission of breast cancer in said patient is an increase in measured BSG levels in the patient and the BSG comprises Mam002 (SEQ ID NO:1).

10. The method of claim 1, 2, 3, 4, or 5 wherein the BSG comprises Mam004 (SEQ ID NO:4).

11. The method of claim 1 wherein the BSG comprises Mam004 (SEQ ID NO:4).

12. The method of claim 1, 2, 3, 4, or 5 wherein the BSG comprises Mam005 (SEQ ID NO:5).

13. The method of claim 1 wherein the BSG comprises Mam005 (SEQ ID NO:5).

\* \* \* \* \*